US00PP08691P

United States Patent [19]

Warriner, deceased

[11] Patent Number: Plant 8,691

[45] Date of Patent: Apr. 19, 1994

[54] MINATURE ROSE PLANT NAMED 'JACHILL'

[75] Inventor: William A. Warriner, deceased, late of Tustin, Calif., by Alene B. Warriner, legal representative

[73] Assignee: Bear Creek Gardens, Inc., Medford, Oreg.

[21] Appl. No.: 23,882

[22] Filed: Feb. 17, 1993

[51] Int. Cl.[5] ..... A01H 5/00

[52] U.S. Cl. ..... Plt./9

[58] Field of Search ..... Plt. 7.1, 9

[56] References Cited

U.S. PATENT DOCUMENTS

Plt. 4898 10/1982 Straun ..... Plt. 9

*Primary Examiner*—Howard J. Locker

*Attorney, Agent, or Firm*—Klarquist, Sparkman, Campbell, Leigh and Whinston

[57] ABSTRACT

A miniature rose having vigorous, dwarf and spreading growth; prolific and recurrent bloom; attractive, dark green, disease-resistant foliage; moderate fragrance; and ease of production from softwood cuttings.

1 Drawing Sheet

The present invention relates to a new and distinct variety of rose plant of the miniature class which was originated by the inventor by crossing the variety Rose Hills Red, with the variety Baby Ophelia.

The primary objective of this breeding was to produce a new rose variety having the dark green, glossy foliage of the female parent combined with the soft pink flowers and fragrance of the male parent. The objective was substantially achieved along with other desirable improvements as evidenced by the following unique combination of characteristics which are outstanding in the new variety and which distinguish it from its parents, as well as from all other varieties:

1. Low, compact and spreading growth habit;
2. Rapid repeat flowering;
3. Dark green, glossy, disease-resistant foliage;
4. Ease of propagation from softwood cuttings; and
5. Moderate fragrance.

Asexual reproduction of this new variety by softwood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—Rose Hills Red.

*Pollen parent.*—Baby Ophelia.

Classification:

*Botanical.*—*Rosa hybrida.*

*Commercial.*—Miniature.

FLOWER

Observations made from specimens grown in a garden environment in Somis, Calif., from March through November, 1992.

Blooming habit: Recurrent.

Bud:

*Size.*—1 inch when the petals start to unfurl.

*Form.*—Short, pointed ovoid.

*Color.*—When sepals first divide, bud color is Red Group 49C. When half blown, the upper sides of the petals are Red Group 49C changing to Red Group 49A in the center of the flower; and the lower sides of the petals are Red Group 49C.

*Sepals.*—Color: Green Group 138B with a bronze overtone. Surface texture: Covered in fine hairs. There are three normally appendaged sepals. There are two unappendaged sepals with hairy edges.

*Receptacle.*—Color: Green Group 137D. Shape: Funnel. Size: Small ($\frac{1}{8}\times\frac{1}{8}$ inch). Surface: Smooth.

*Peduncle.*—Length: Short ($\frac{1}{2}$–1 inch). Surface: Smooth. Color: Medium green and bronzy. Strength: Stiff, erect, slender.

Bloom:

*Size.*—Small. Average open size is 2 inches.

*Borne.*—Singly and several together, in clusters. If in clusters: Rounded.

*Stems.*—Short (6–8 inches).

*Form.*—When first open: High centered. Permanence: Retains its form to the end, outer petals curl back.

*Petalage.*—Number of petals under normal conditions: 25–30.

*Color.*—The upper side of the petals is Red Group 49C on the outer, fully exposed petals; Red Group 49A on the inner, protected petals. The reverse side of the petals is Red Group 49C. The base of each petal has a very small ($\frac{1}{8}\times\frac{1}{8}$ inch) greenish white half moon at the point of attachment. The major color on the upper side is Red Group 49C.

*Variegations.*—Some discoloration and an occasional green streak on the guard petals.

*Discoloration.*—The general tonality at the end of the first day: No change. At the end of the third day: As the flower opens and more petals are exposed to the sun, the flower becomes more Red Group 49C in color and less Red Group 49A.

*Fragrance.*—Moderate.

Petals:

*Texture.*—Thick.
*Shape.*—Deltoid.
*Form.*—Tips slightly recurved, edges slightly quilled.
*Arrangement.*—Imbricated, with few petaloids in the center.
*Persistence.*—Drop off cleanly.
*Lastingness.*—On the plant: Fair (5 days). As a cut flower: Fair (6 days).

Reproductive parts:
*Anthers.*—Size: Small. Quantity: Many. Color: Yellow. Arrangement: Regular around styles.
*Filaments.*—Color: White.
*Pollen.*—Color: Lemon yellow.
*Styles.*—Color: White.
*Stigmas.*—Color: Greenish white.

Form: Bush.

Growth: Vigorous, dwarf, branching and spreading.

Foliage:
*Number of leaflets on normal mid-stem leaves.*—5 or 7.
*Size.*—Small (3×2 inches).
*Quantity.*—Abundant.
*Color.*—New foliage: Dark green with some reddish cast on lower surface. Old foliage: Dark green, glossy. Green Group 135A.

Leaflets:
*Shape.*—Pointed oval.
*Texture.*—Upper side: Leathery, glossy.

*Edge.*—Serrated.
*Serration.*—Single, small.
*Petiole rachis.*—Color: Reddish.
*Petiole underside.*—Smooth, with occasional prickles.
*Stipules.*—Short (⅜ inch long), serrated, bearded.
*Disease resistance.*—Resistant to mildew and rust under normal growing conditions at Somis, Calif.

Wood:
*New wood.*—Color: Reddish green. Bark: Smooth.
*Old wood.*—Color: Green. Bark: Smooth.

Prickles:
*Quantity.*—On main canes from base: Ordinary. On laterals from main canes: Ordinary.
*Form.*—Short, hooked downward.
*Color when young.*—Red.

Small prickles:
*Quantity.*—None on main stalks or on laterals.

It is claimed:

1. A new and distinct variety of rose plant of the miniature class, substantially as herein shown and described, characterized particularly as to novelty by the unique combination of its vigorous, dwarf and spreading growth; prolific and recurrent bloom; attractive, dark green, disease-resistant foliage; moderate fragrance; and ease of production from softwood cuttings.

* * * * *

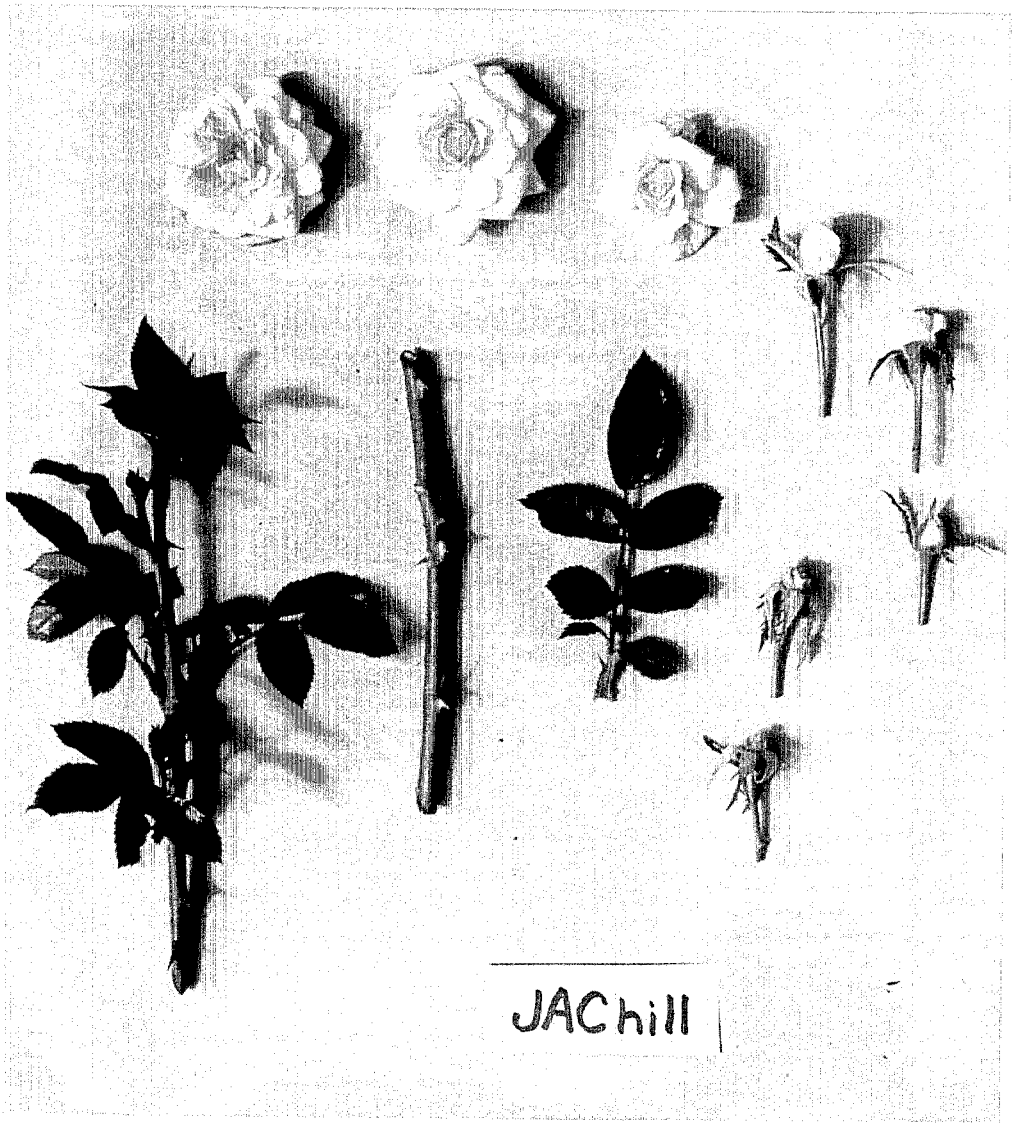
JAChill